United States Patent [19]
Murrer et al.

[11] Patent Number: 5,651,939
[45] Date of Patent: Jul. 29, 1997

[54] METHOD AND APPARATUS FOR IMPROVING LIQUID FLOW

[75] Inventors: Edwin William John Murrer, Bucks; Philip Peter Butler, Essex; Sin-Man Lo, Oxon, all of England

[73] Assignee: Anglian Water Services, Inc., Huntingdon, England

[21] Appl. No.: 661,766

[22] Filed: Jun. 11, 1996

Related U.S. Application Data

[63] Continuation of Ser. No. 274,506, Jul. 13, 1994, abandoned.

[30] Foreign Application Priority Data

Jul. 14, 1993 [GB] United Kingdom ............... 9314592

[51] Int. Cl.⁶ ........................................... A61L 2/00
[52] U.S. Cl. ........................ 422/28; 261/123; 261/122.1; 261/DIG. 42; 422/1; 422/37; 422/224; 422/231
[58] Field of Search .................... 422/1, 28, 37, 422/22, 186.07, 224, 228, 231, 236, 305; 261/123, 122.1, DIG. 42; 210/760, 199, 230, 320

[56] References Cited

U.S. PATENT DOCUMENTS

| | | | |
|---|---|---|---|
| 3,276,994 | 10/1966 | Andrews | 210/760 X |
| 3,764,014 | 10/1973 | Stern et al. | 210/220 |
| 3,945,918 | 3/1976 | Kirk | 210/760 X |
| 4,507,253 | 3/1985 | Wiesmann | 261/123 X |
| 4,680,111 | 7/1987 | Ueda | 210/199 X |
| 5,053,140 | 10/1991 | Hurst | 210/760 X |
| 5,180,499 | 1/1993 | Hinson et al. | 210/760 X |
| 5,348,664 | 9/1994 | Kim et al. | 210/760 X |

FOREIGN PATENT DOCUMENTS

| | | |
|---|---|---|
| 3433175A | 3/1986 | Germany . |
| 60-153988 | 8/1985 | Japan . |
| 4035790 | 2/1992 | Japan . |
| 4322705 | 11/1992 | Japan . |
| 2149080 | 6/1985 | United Kingdom . |

*Primary Examiner*—Robert J. Warden
*Assistant Examiner*—E. Leigh Dawson
*Attorney, Agent, or Firm*—Wigman, Cohen, Leitner & Myers, P.C.

[57] ABSTRACT

Especially for use in disinfecting water by bubbling in a gas such as ozone, novel apparatus having an inlet and an outlet for liquid and which defines a flow path therebetween, the path including, in succession, a downward flow zone and an upward flow zone, the zones being separated by a wall beneath which there is a gap for the flow between the zones, wherein the upward flow zone includes a perforate baffle, adjacent to the gap, such that there is substantially laminar flow throughout that zone.

10 Claims, 2 Drawing Sheets

METHOD AND APPARATUS FOR IMPROVING LIQUID FLOW

This is a continuation of application Ser. No. 08/274,506, filed Jul. 13, 1994, abandoned.

FIELD OF THE INVENTION

This invention relates to a method for improving flow conditions in a tank, and to apparatus adapted for such improvement.

BACKGROUND OF THE INVENTION

Many systems are known, which involve gas/liquid contact, e.g. for the aerobic digestion of biomass, using oxygen or air, and for the disinfection of water, using chlorine or, increasingly ozone. These systems are generally based on the principle of introducing bubbles of the gas into the liquid, e.g. in counter-current, with a view to maximising the degree of contact between the active gas and the liquid.

A known water disinfection tank comprises an inlet and an outlet for liquid and defines a flow plath including, in succession, a downward flow or diffuser zone including a gas bubble inlet (e.g. for chlorine or ozone gas) and an upward flow or decay zone, the zones being separated by a wall beneath which there is a gap for the flow between these zones. The final decay zone is a relatively large chamber, in which it is intended that all residual disinfectant should stay in contact with the liquid for a specified time, before passing to the outlet of the apparatus. Prolonged contact is necessary, in order effectively to kill organisms such as Giardia.

SUMMARY OF THE INVENTION

It has now been discovered that the efficiency of such apparatus can be improved, with consequent savings in the cost of expensive materials such as ozone, if the apparatus is modified by introducing a perforate baffle into the decay zone.

In particular, it has been found that the final decay chamber in a water disinfection tank is usually dominated by a large recirculating flow. The chamber is therefore not fully utilised, and indeed there may be the quite unsatisfactory combination of liquid circulating for an extended period in the chamber while other liquid and ozone or other disinfectant pass almost immediately to the outlet. This problem is overcome by the use of a perforate baffle, that ensures substantially laminar flow throughout the chamber.

BRIEF DESCRIPTION OF THE DRAWINGS

The invention will now be described by way of example only with reference to the accompanying drawings, in which.

DESCRIPTION OF THE INVENTION

Figure 1:
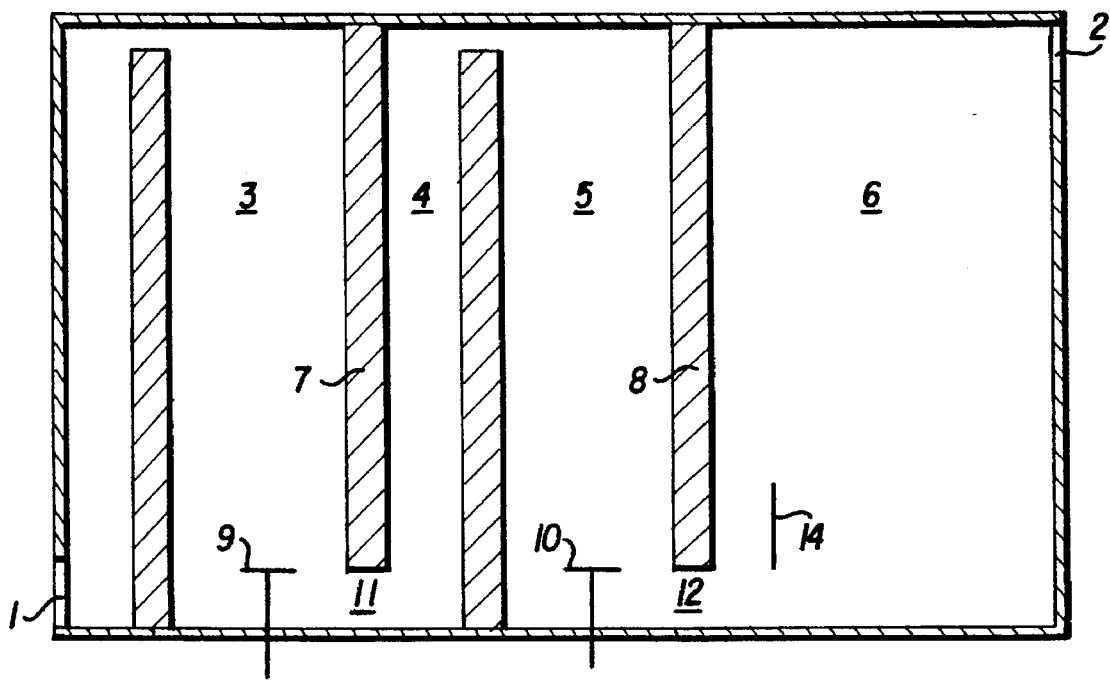
FIG. 1 is a schematic cross-section view of apparatus embodying the invention more particularly described in the copending, commonly-assigned U.S. patent application (Ser. No. 08/274,505, currently pending), made by Sin-Man Lo, having the same filing date, and entitled "Method and Apparatus for Gas/Liquid Contact"

In the case where gaseous disinfectant is introduced in an earlier zone, and then through any desired combination of downward (diffuser) and upward (decay) flow zones, it may be desirable that no bubbly flow is carried into final decay chamber, in order that the decay of the dissolved gas, e.g. ozone, does not affect the water flow. It is then necessary only to consider the single phase water flow through the chamber. The removal of bubbly flow, by the provision of raised gas bubble inlets, is the subject of said copending Application. This single phase water flow through the chamber is the distinguishing characteristic feature of FIG. 1, which shows apparatus comprising an inlet 1 and outlet 2 between which a flow path is defined, comprising a first diffuser zone 3, a first decay zone 4, a second diffuser zone 5 and a final decay zone 6. The respective first zones are separated by a wall 7 and the respective second zones by a wall 8. Towards the base, but raised above that, in each of the diffuser zones, are gas diffusers 9 and 10, each at the height of the respective flow gaps 11 and 12.

The perforate plate 14 may have a length that is substantially the same as the height of the flow gap 12. A perforate baffle 14 may preferably be installed in the second decay zone 6 for the reasons discussed hereafter in connection with the description of FIG. 2. The perforate baffle 14 may preferably be adjacent to the flow gap 11 between the wall 7 and the floor of the apparatus.

It will be readily appreciated that the "wall" is not necessarily of thin cross-section. The term "wall" is used merely to define the fact that there are discrete diffuser and decay zones, with a channel for liquid flow between them.

Figure 2:
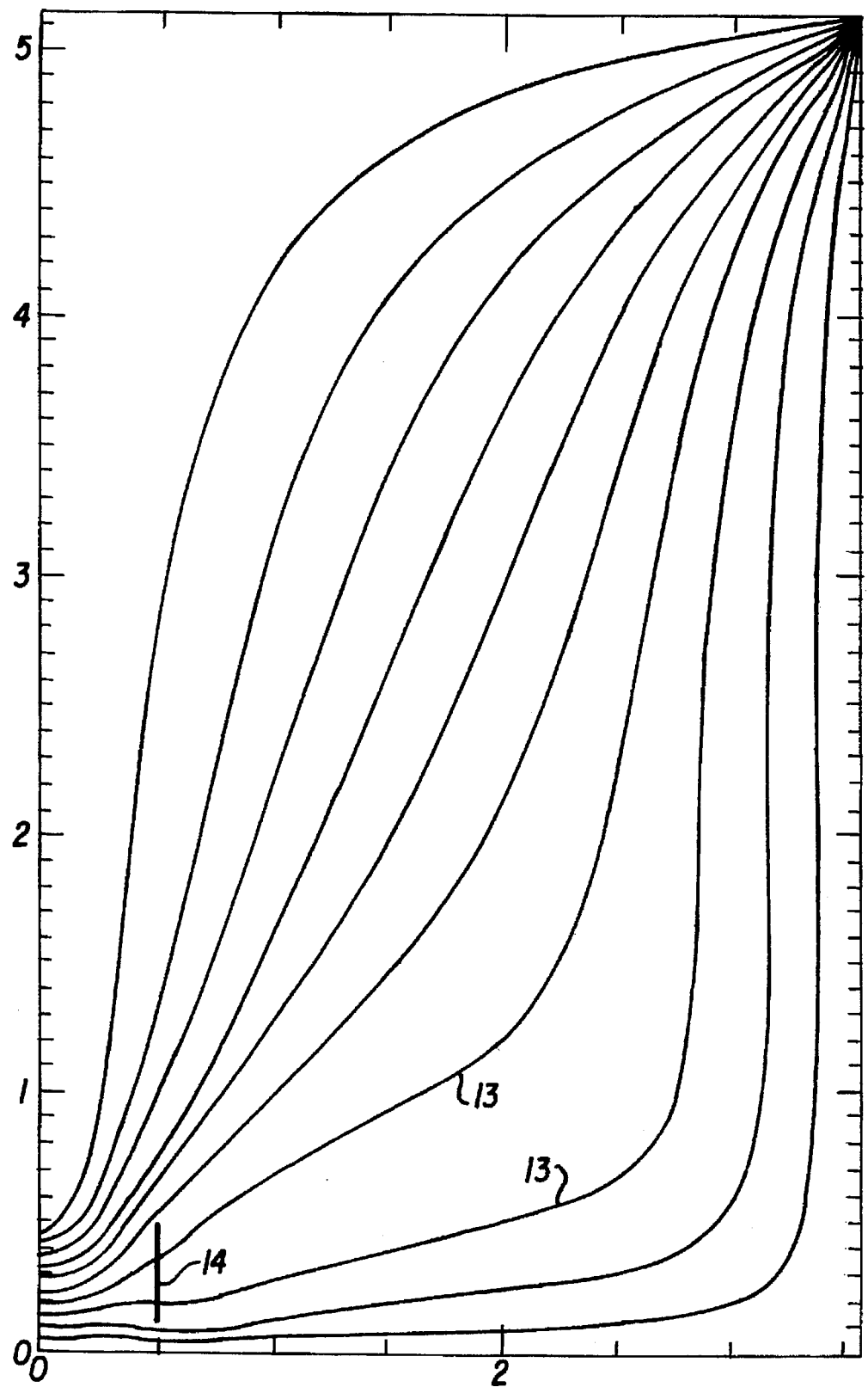
FIG. 2 shows schematically (the scales are for illustration only) liquid flow vectors between an inlet at the bottom left and an outlet at the top right, of a decay chamber in disinfection apparatus of the general type shown in FIG. 1 and more specifically described in said copending plug or laminar flow that is shown.

The streamlines 13 shown in FIG. 2 are evenly distributed, indicating a relatively uniform flow through the chamber. The theoretical model of the flow has been shown to be correct, using salt traces. The effect was duplicated at different flow rates, one approximately twice the other. The drawing indicates that reasonably welldistributed flow may be obtained by installing a perforate baffle 14 with an area porosity of 0.3 and a height of 0.4 m placed vertically, 0.4 m away from the inlet and 0.1 m above the floor.

In summary, it is generally preferred that the baffle is substantially vertical. It is preferably positioned above the floor of the upward flow zone. It is also preferred that the distance of the baffle from the gap is substantially the same as the height of the gap. The use of the word "substantially" indicates that the dimensions are within 100%, and preferably within 50%, of each other. The preferred area porosity of the baffle is 0.1–0.6 m, and preferably within the terms of a baffle as defined herein.

What we claim is:

1. Apparatus comprising an enclosure having a floor and an inlet and an outlet for liquid and a flow path therebetween, said flow path including, in succession, a downward flow zone and an upward flow zone, said zones being separated by a wall spaced away from said enclosure between which a gap is formed by a space between said floor and said wall for the flow between the zones, wherein the upward flow zone includes a perforate baffle having a length, adjacent to said gap, constructed and arranged such that there is substantially laminar flow throughout that zone.

2. Apparatus according to claim 1, in which said baffle is substantially vertical.

3. Apparatus according to claim 1, in which said baffle is positioned above the floor of said enclosure in said upward flow zone.

4. Apparatus according to claim 1, in which the length of said baffle is substantially the same as the space between said floor and said wall which forms said gap.

5. Apparatus according to claim 1, in which the baffle is spaced away from said gap substantially the same distance as the space between said floor and said wall which forms said gap.

6. Apparatus according to claim 1, which comprises a gas bubble inlet in said downward flow zone.

7. A method for disinfecting water, which comprises passing the water through apparatus comprising an enclosure having a floor and an inlet and an outlet for liquid and a flow path therebetween, said flow path including, in succession, a downward flow zone and an upward flow zone, said zones being separated by a wall spaced away from said enclosure beneath which a gap is formed by a space between said floor and said wall for the flow between the zones, wherein the upward flow zone includes a perforate baffle, adjacent to said gap, such that there is substantially laminar flow throughout that zone, and introducing a disinfectant into the water in said downward flow zone.

8. A method according to claim 7, in which the disinfectant is ozone or chlorine.

9. A method for disinfecting water, which comprises passing the water through apparatus comprising an enclosure having a floor and an inlet and an outlet for liquid and a flow path therebetween, said flow path including, in succession, a downward flow zone and an upward flow zone, said zones being separated by a wall spaced away from said enclosure beneath which a gap is formed by a space between said floor and said wall for the flow between the zones, wherein the upward flow zone includes a perforate baffle, adjacent to said gap, such that there is substantially laminar flow throughout that zone, and introducing bubbles of a gaseous disinfectant into said downward flow zone.

10. A method according to claim 8, in which the disinfectant ozone or chlorine.

* * * * *